(12) United States Patent
Matsumoto et al.

(10) Patent No.: US 10,016,121 B2
(45) Date of Patent: Jul. 10, 2018

(54) ULTRASOUND TRANSDUCER ELEMENT AND ULTRASOUND ENDOSCOPE

(71) Applicants: OLYMPUS MEDICAL SYSTEMS CORP., Tokyo (JP); OLYMPUS CORPORATION, Tokyo (JP)

(72) Inventors: Kazuya Matsumoto, Nagano (JP); Kazuhisa Karaki, Shiojiri (JP); Mamoru Hasegawa, Nagano (JP); Katsuhiro Wakabayashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1074 days.

(21) Appl. No.: 14/265,745

(22) Filed: Apr. 30, 2014

(65) Prior Publication Data

US 2014/0236018 A1    Aug. 21, 2014

Related U.S. Application Data

(63) Continuation of application No. PCT/JP2012/068603, filed on Jul. 23, 2012.

(30) Foreign Application Priority Data

Nov. 1, 2011    (JP) .................................. 2011-240475

(51) Int. Cl.
    *B06B 1/02*    (2006.01)
    *H02N 1/00*    (2006.01)
    (Continued)

(52) U.S. Cl.
    CPC ............... *A61B 1/015* (2013.01); *A61B 8/12* (2013.01); *A61B 8/445* (2013.01); *A61B 8/4494* (2013.01);
    (Continued)

(58) Field of Classification Search
    CPC ............................................... H02N 1/00–1/12
    (Continued)

(56) References Cited

U.S. PATENT DOCUMENTS

| | | | |
|---|---|---|---|
| 5,081,995 A * | 1/1992 | Lu ........................ | G10K 11/341 310/369 |
| 2001/0020320 A1* | 9/2001 | McIntosh .............. | B81B 3/0086 29/25.41 |

(Continued)

FOREIGN PATENT DOCUMENTS

| JP | 2005-510264 A | 4/2005 |
|---|---|---|
| JP | 2006-122344 A | 5/2006 |

(Continued)

OTHER PUBLICATIONS

English abstract only of International Patent Publication No. WO 03/011749 A2 dated Feb. 13, 2003.

(Continued)

*Primary Examiner* — Thomas Truong
(74) *Attorney, Agent, or Firm* — Scully, Scott, Murphy & Presser, P.C.

(57) ABSTRACT

An ultrasound transducer element includes a plurality of electrostatic capacitance type ultrasound cells each having a lower electrode portion and a membrane including an upper electrode portion that are oriented and disposed via a cavity circular in plan view, and a thickness of the cavity monotonously decreases in a curved manner toward an outer circumferential portion from a center portion of the cavity.

12 Claims, 7 Drawing Sheets

(51) Int. Cl.
    *A61B 8/00*     (2006.01)
    *A61B 1/015*     (2006.01)
    *A61B 8/12*     (2006.01)

(52) U.S. Cl.
    CPC ............ *A61B 8/461* (2013.01); *B06B 1/0292* (2013.01); *H02N 1/00* (2013.01)

(58) Field of Classification Search
    USPC ........... 310/300, 309; 600/459, 437; 73/718, 73/514.32
    See application file for complete search history.

(56) References Cited

U.S. PATENT DOCUMENTS

2006/0004289 A1* 1/2006 Tian ...................... B06B 1/0292
    600/459

2007/0161896 A1* 7/2007 Adachi ................. B06B 1/0292
    600/437
2011/0068654 A1* 3/2011 Cheng ................... B06B 1/0292
    310/300

FOREIGN PATENT DOCUMENTS

| | | |
|---|---|---|
| JP | 2009-055474 A | 3/2009 |
| JP | 2011-155345 A | 8/2011 |
| WO | 20091077961 A2 | 6/2009 |

OTHER PUBLICATIONS

International Search Report dated Aug. 21, 2012 issued in PCT/JP2012/068603.

Extended Supplementary European Search Report dated Jul. 3, 2015 from related European Application No. 12 84 4742.2.

* cited by examiner

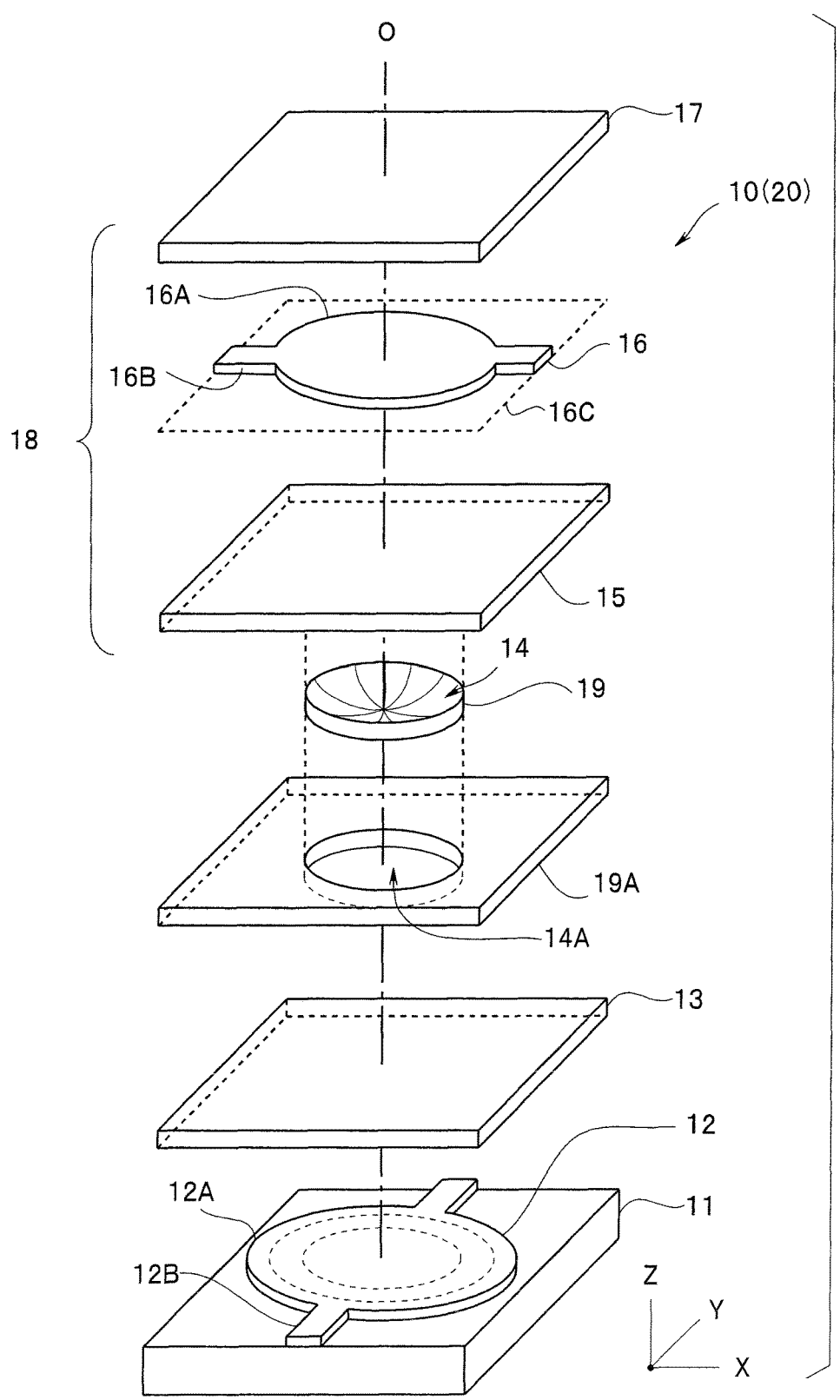

ULTRASOUND TRANSDUCER ELEMENT AND ULTRASOUND ENDOSCOPE

CROSS REFERENCE TO RELATED APPLICATION

This application is a continuation application of PCT/JP2012/068603 filed on Jul. 23, 2012 and claims benefit of Japanese Application No. 2011-240475 filed in Japan on Nov. 1, 2011, the entire contents of which are incorporated herein by this reference.

BACKGROUND OF INVENTION

1. Field of the Invention

The present invention relates to an electrostatic capacitive type ultrasound transducer element and an ultrasound endoscope including the ultrasound transducer element.

2. Description of the Related Art

An ultrasound diagnostic method that irradiates an inside of a body with ultrasound, and images a state of the inside of the body from an echo signal to perform diagnosis is widespread. One of the ultrasound diagnostic apparatuses for use in the ultrasound diagnostic method is an ultrasound endoscope (hereinafter, called "a US endoscope"). In a US endoscope, an ultrasound transducer is placed at a distal end rigid portion of an insertion portion that is introduced into an inside of a body. An ultrasound transducer has a function of converting an electric signal into ultrasound and transmitting the ultrasound to the inside of a body, and receiving ultrasound reflected in the inside of the body and converting the ultrasound into an electric signal.

For an ultrasound transducer, a ceramic piezoelectric material containing lead that has large environmental load, for example, PZT (lead zirconate titanate) is mainly used. In contrast with this, development of an electrostatic capacitance type ultrasonic transducer (capacitive micro-machined ultrasonic transducer; hereinafter, called "a c-MUT") that does not contain lead in the material and is produced with use of MEMS (micro electro mechanical systems) technique is being advanced.

As is disclosed in Japanese Patent Application Laid-Open Publication No. 2005-510264, a c-MUT has an ultrasound cell (hereinafter, called "a US cell") in which an upper electrode portion and a lower electrode portion are disposed to face each other via a cavity portion (cavity) as a unit element. In the US cell, a membrane including the upper electrode portion on an upper side of the cavity configures a vibration portion. A plurality of US cells with the respective electrode portions connected by a wiring portion are arranged to configure an ultrasound transducer element (hereinafter, called "a US element").

The US cell vibrates the membrane including the upper electrode portion by an electrostatic force by application of a voltage to between the lower electrode portion and the upper electrode portion to generate ultrasound. Further, when ultrasound is incident on the membrane from an outside, the membrane deforms to change a spacing of both the electrode portions, and therefore, the ultrasound is converted into an electric signal from a change in electrostatic capacitance.

SUMMARY OF THE INVENTION

An ultrasound transducer element of an embodiment of the present invention includes a plurality of electrostatic capacitance type ultrasound cells each having a lower electrode portion and a membrane including an upper electrode portion that are oriented and disposed via a cavity circular in plan view, wherein a thickness of the cavity monotonously decreases in a curved manner toward an outer circumferential portion from a center portion of the cavity.

Further, an ultrasound endoscope of another embodiment includes an ultrasound transducer element having a plurality of electrostatic capacitance type ultrasound cells each having a lower electrode portion and a membrane including an upper electrode portion that are oriented and disposed via a cavity circular in plan view, wherein a thickness of the cavity monotonously decreases in a curved manner toward an outer circumferential portion from a center portion of the cavity.

BRIEF DESCRIPTION OF THE DRAWINGS

FIG. 6 is an exploded view of an ultrasound cell of the ultrasound transducer element of the first embodiment;

DETAILED DESCRIPTION OF THE PREFERRED EMBODIMENT(S)

First Embodiment

Hereinafter, an ultrasound transducer element (a US element) 20 of a first embodiment, and an ultrasound endoscope (hereinafter, called "a US endoscope") 2 having the US element 20 will be described with reference to the drawings.

<Configuration of Ultrasound Endoscope>

Figure 1:
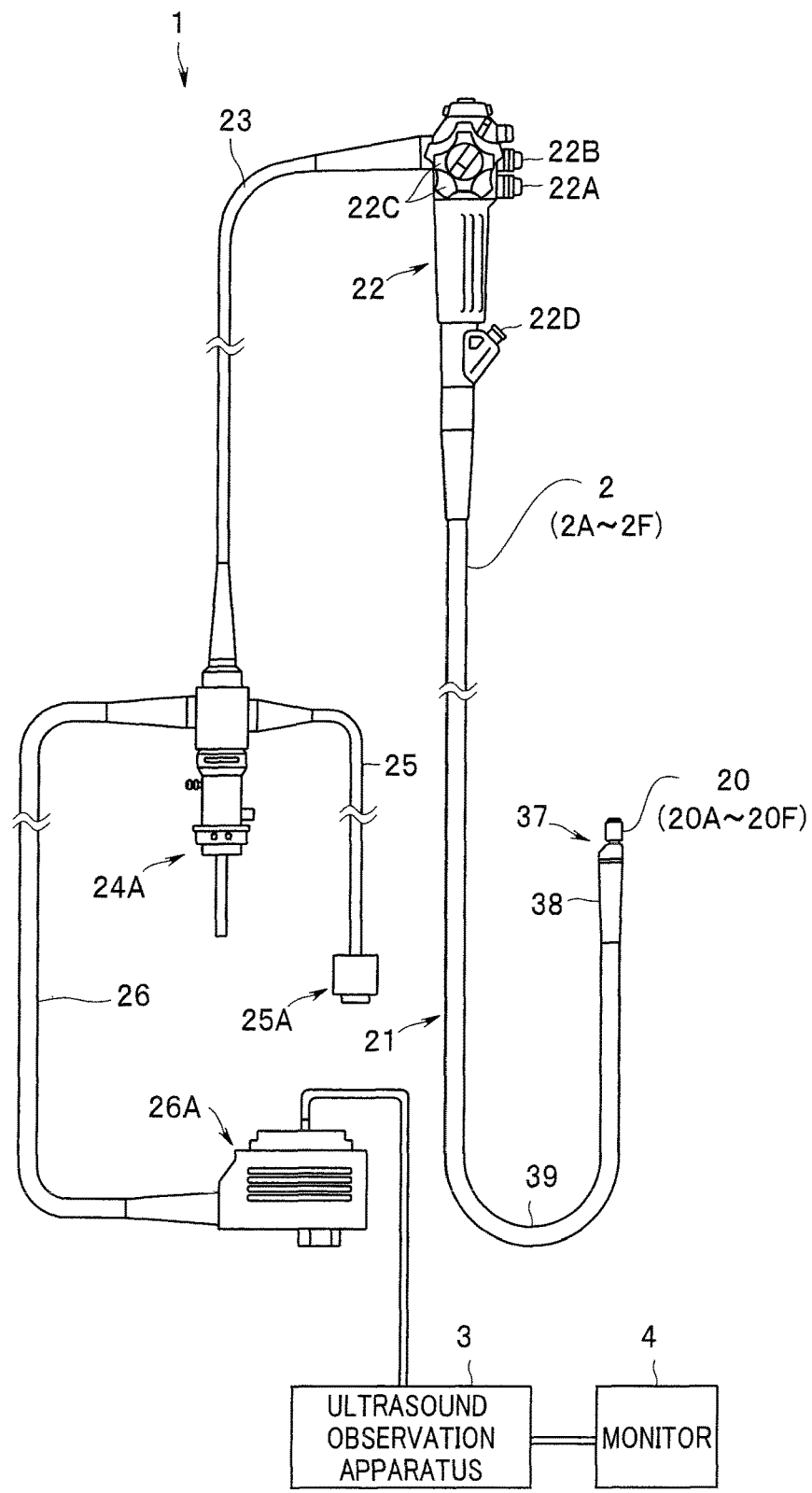
FIG. 1 is an outside view for explaining an endoscope system including an ultrasound endoscope of a first embodiment.

As shown in FIG. 1, the US endoscope 2 configures an ultrasound endoscope system 1 with an ultrasound observation apparatus 3 and a monitor 4. The US endoscope 2 includes an elongated insertion portion 21 that is inserted into a body, an operation portion 22 that is arranged at a proximal end of the insertion portion 21, and a universal cord 23 that is extended from a side portion of the operation portion 22.

At a proximal end portion of the universal cord 23, a connector 24A that is connected to a light source apparatus (not illustrated) is placed. From the connector 24A, a cable 25 that is detachably connected to a camera control unit (not illustrated) via a connector 25A, and a cable 26 that is detachably connected to the ultrasound observation apparatus 3 via a connector 26A are extended. The monitor 4 is connected to the ultrasound observation apparatus 3.

The insertion portion 21 is configured by a distal end rigid portion (hereinafter, called "a distal end portion") 37, a bending portion 38 that is located at a rear end of the distal end portion 37, and a flexible tube portion 39 that is located at a rear end of the bending portion 38 to reach the operation portion 22, and has a small diameter, a long length and flexibility being connectively provided in sequence from a distal end side. At a distal end side of the distal end portion 37, an ultrasound unit (a US unit) 30 that is an ultrasound transmitting and receiving portion is placed.

At the operation portion 22, an angle knob 22A that performs bending control of the bending portion 38 in a desired direction, an air/water feeding button 22B that performs air feeding and water feeding operations, a suction button 22C that performs a suction operation, a treatment instrument insertion port 22D to be an inlet port for a treatment instrument that is introduced to an inside of a body and the like are placed.

Figure 2:
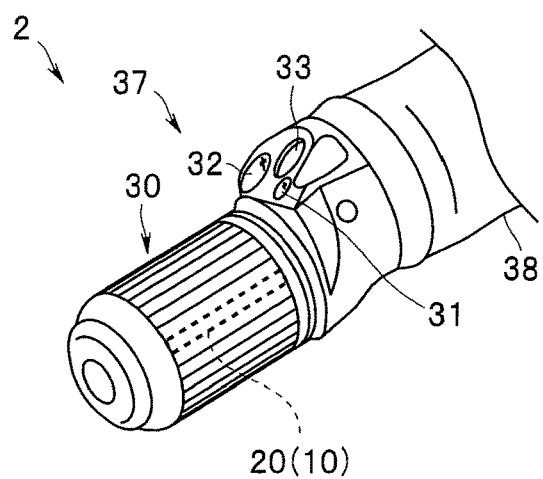
FIG. 2 is a perspective view for explaining a distal end portion of the ultrasound endoscope of the first embodiment.

As shown in FIG. 2, at the distal end portion 37 at which the US unit 30 that transmits and receives ultrasound is provided, an illumination lens cover 31 that configures an illumination optical system, an observation lens cover 32 of an observation optical system, a forceps port 33 also used as a suction port, and an air/water feeding nozzle not illustrated are placed.

Figure 3:
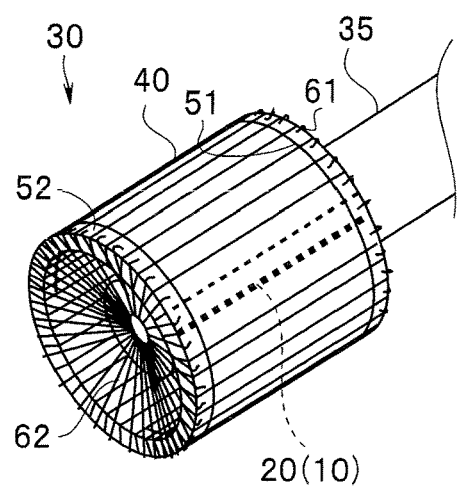
FIG. 3 is a perspective view for explaining a configuration of an ultrasound unit of the ultrasound endoscope of the first embodiment.

As shown in FIG. 3, an ultrasound array (a US array) 40 of the US unit 30 is a radial type transducer group in which long sides of a plurality of US elements 20 rectangular in plan view are connected and disposed to bend in a cylindrical shape. Namely, in the US array 40, 64 of the US elements 20 each with a short side of 0.1 mm or less are placed on a side surface of a cylinder with a diameter of 2 mm, for example.

Note that the US array 40 is a radial type transducer group, but the US array may be a convex type transducer group that is bent into a convex shape.

<Configuration of Ultrasound Transducer Element>

Figure 4:
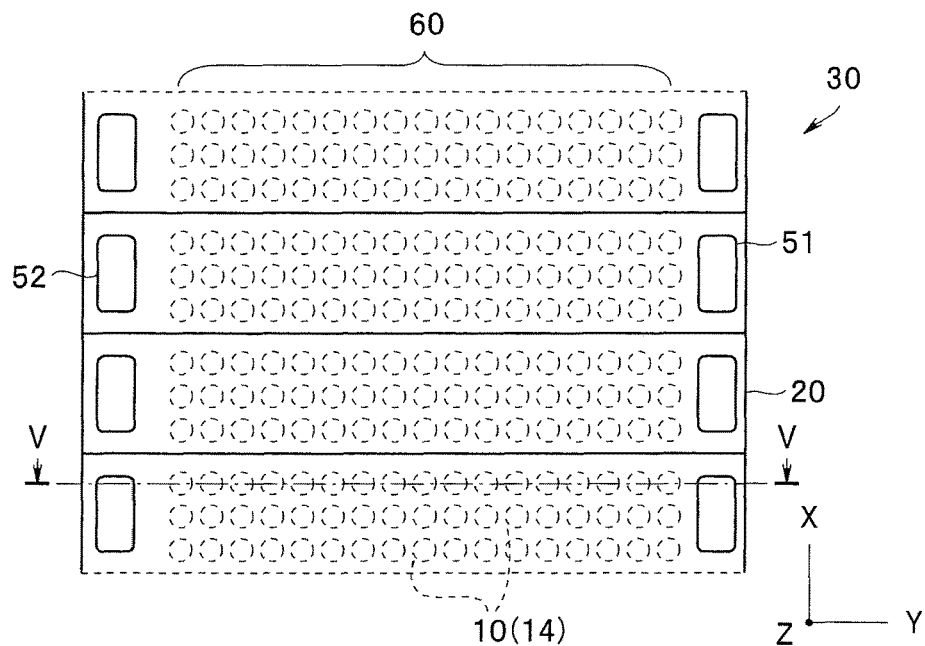
FIG. 4 is a top view for explaining a configuration of an ultrasound transducer element of the first embodiment.

As shown in FIG. 4, the ultrasound transducer element 20 that is rectangular in plan view has a transmission and reception portion 60 in which a plurality of ultrasound cells 10 are two-dimensionally disposed in a matrix shape. In each of the US elements 20, an upper electrode terminal 51 and a lower electrode terminal 52 for driving the plurality of ultrasound cells 10 are placed. The plurality of US elements 20 have respective long sides connected to one another.

Note that the drawings are all schematic views for explanation, and the numbers, the shapes, the thicknesses, and the dimensions of the patterns and the ratios of the sizes and the like differ from reality.

<Basic Structure of Ultrasound Cell>

Figure 5:
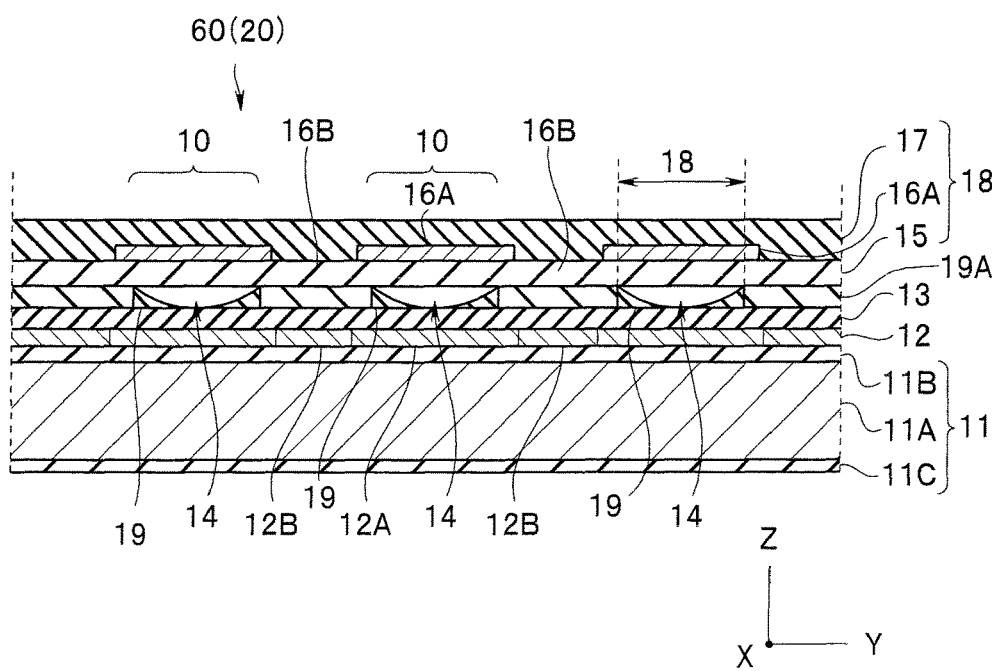
FIG. 5 is a partial sectional view taken along a V-V line in FIG. 4.

As shown in FIG. 5 and FIG. 6, in each of the respective US cells 10, a lower electrode portion 12A and an upper electrode portion 16A are disposed to face each other via a lower insulating layer 13, a gap adjusting portion 19, a cavity 14 and an upper insulating layer 15. Note that hereinafter, a substrate side in a Z direction will be called a lower side, and a protection layer 17 side will be called an upper side.

Namely, the US cell 10 has the lower electrode layer 12, the lower insulating layer 13, a gap adjusting layer 19A having the cavity 14, the upper insulating layer 15, the upper electrode layer 16 and the protection layer 17 that are stacked in sequence on a substrate 11 formed from silicon that is a base. A part 15B of the upper insulating layer 15 to the protection layer 17 that are directly over the cavity 14 configure a membrane 18. Note that the membrane 18 is illustrated to be thick for explanation in FIG. 6 and the like, but is a vibration film of a small thickness of 1 μm to 10 μm, for example, which is stretched over an opening of the cavity 14 which is circular in plan view.

The lower electrode layer 12 is formed by the lower electrode portion 12A and a lower wiring portion 12B. Further, the upper electrode layer 16 is formed by the upper electrode portion 16A and an upper wiring portion 16B. The lower electrode portions 12A of all of the plurality of US cells 10 of the US element 20 are connected to the lower electrode terminal 52 via the lower wiring portions 12B. Similarly, the upper electrode portions 16A of all of the plurality of US cells 10 of the US element 20 are connected to the upper electrode terminal 51 via the upper wiring portions 16B.

Note that the lower electrode portion 12A, the upper electrode portion 16A, the gap adjusting portion 19 and the cavity 14 are in rotationally symmetrical shape with respect to a center axis O, and are circular in plan view.

The gap adjusting portion 19 that adjusts a gap that is a thickness (height) of the cavity 14, and is formed from a material with a high dielectric constant is placed on the lower insulating layer 13 in an inside of a cavity forming portion 14A that is a cylindrical cavity portion. In other words, a space of the cavity forming portion 14A that does not have the gap adjusting portion 19 is the cavity 14. A thickness "T" of the gap adjusting portion 19 is, for example, 0 (μm) that is the smallest in a center portion, and monotonously increases in a curved manner toward an outer circumferential portion from the center portion.

Namely, distribution $T(r)$ of the thickness "T" of the gap adjusting portion 19 with a radius of "R" can be expressed by a function that is shown in (equation 1), for example, and monotonously increases in a curved manner toward the outer circumferential portion from the center portion. Here, a distance from the center axis O is "r", and a thickness of an outer periphery ($r=R$) of the gap adjusting portion 19 is "TR". As a matter of course, the distribution T(r) does not have to correspond to the function shown in (equation 1) completely, and may have a little difference, for example, a difference of approximately ±5%.

$$T(r)=TR\times[1-J0(2.4/R\times r)] \quad \text{(Equation 1)}$$

J0 represents a Bessel function of the order 0, J0(0)=1 and J0(2.4)=0.

Here, (equation 1) is an expression using a Bessel function of the zeroth kind that shows an envelope of vibration of a circular plane vibration plate the outer periphery of which is restrained.

The gap adjusting portion 19 is preferably formed from a material with a high dielectric constant, for example, $SiO_2$ (Ks=3.8) with a relative dielectric constant Ks being 3 or more, and especially preferably formed from SiN, for example, with a relative dielectric constant Ks being 5 or more. As a matter of course, $Al_2O_3$ (Ks=8.5), $Ta_2O_5$ (Ks=20 to 25), $TiO_2$ (Ks=40 to 110), HfOF, or $HfO_2$, and further barium titanate ceramics or the like, which has a higher dielectric constant Ks, may be used, and from the viewpoint of easiness of a forming method and the like, the upper limit of the relative dielectric constant Ks is approximately 150.

A thickness (height) "t" of the cavity 14 monotonously decreases in a curved manner toward the outer circumferential portion from a center O of the cavity 14 in response to thickness distribution of the gap adjusting portion 19, and is expressed by a Bessel function t(r) of the zeroth kind shown in (equation 2). Namely, the cavity 14 is in a so-called downward convex shape. Note that "t0" represents a thickness (height) "t" at the center (r=0) of the cavity 14, and equals to the thickness "TR" of the outer periphery (r=R) of the gap adjusting portion 19.

$$t(r)=t0\times J0(2.4/R\times r) \quad \text{(Equation 2)}$$

Namely, the thickness distribution (variation state) t(r) of the thickness "t" of the cavity 14 is the same as a theoretical deformation state of the membrane 18 when driven.

Next, with use of FIG. 7A to FIG. 7E, a method for producing the US element 20 will be described.

<Formation of Lower Electrode Layer>

A conductive layer formed from conductive silicon or a metal, for example, copper, gold, Mo, Ta or aluminum is deposited on an entire surface of the substrate 11 on which an insulating layer (not illustrated) is formed by a sputtering method, a CVD (chemical vapor deposition) method or the like. Subsequently, after a mask pattern formed from resist is formed on the conductive layer by photolithography, the conductive layer which is not covered with the mask pattern is selectively removed by etching, and thereby, the lower electrode layer 12 is formed.

<Formation of Lower Insulating Layer>

The lower insulating layer 13 formed from an insulating material such as SiN is deposited in such a manner as to cover the lower electrode layer 12 by a CVD method, for example. In accordance with necessity, a surface of the lower insulating layer 13 is flattened by a CMP (chemical mechanical polish) method after deposition. Subsequently, an intermediate insulating layer 15A foamed from SiN, for example, is further formed on the lower insulating layer 13. A thickness "t0 (TR)" of the intermediate insulating layer 15A corresponds to a thickness (height) of the cavity forming portion 14A.

Figure 7A:
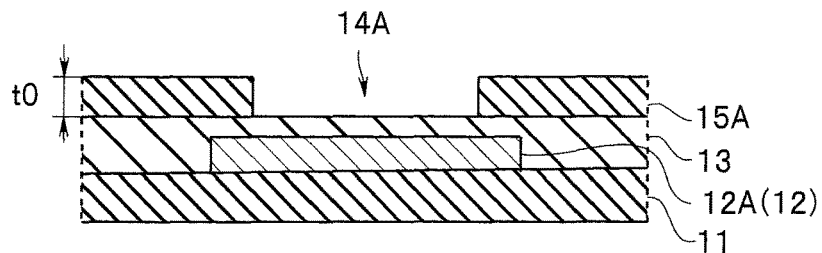
FIG. 7A is a partial sectional view for explaining a method for producing the ultrasound transducer element of the first embodiment.

As shown in FIG. 7A, with use of a mask produced by a photolithography method, the intermediate insulating layer 15A is selectively removed by etching and the cavity forming portion 14A is formed. When the lower insulating layer 13 and the intermediate insulating layer 15A are formed from different materials, etching is performed with a chemical solution, gas or the like that selectively etches the intermediate insulating layer 15A. When the lower insulating layer 13 and the intermediate insulating layer 15A are formed from the same material, for example, SiN, the surface of the intermediate insulating layer 15A is flattened by a CMP method in accordance with necessity, after which, only the cavity forming portion 14A may be etched until the cavity forming portion 14A has a maximum height (depth) "t0" of the cavity 14, based on an etching rate of the intermediate insulating layer 15A.

<Formation of Gap Adjusting Portion>

The gap adjusting layer 19A formed from a material with a high dielectric constant is deposited on the surface of the intermediate insulating layer 15A to have a maximum thickness (height) "TR (t0)" of the cavity forming portion 14A, or more. Subsequently, a portion corresponding to a film thickness (convex portion) of the gap adjusting layer 19A is polished by a CMP method and a surface is flattened. Thereupon, a structure in which the gap adjusting layer 19A is buried only in the inside of the cavity forming portion 14A is produced.

Figure 7B:
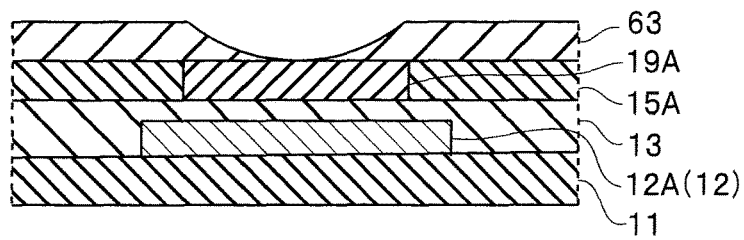
FIG. 7B is a partial sectional view for explaining the method for producing the ultrasound transducer element of the first embodiment.

As shown in FIG. 7B, a photoresist is exposed via a gray scale photo-mask or the like, and thereby a resist mask 63 in which a thickness monotonously increases toward the outer circumferential portion from the center portion is produced. Namely, the thickness of the resist mask 63 monotonously increases in a curved manner toward the outer circumferential portion from the center portion as shown by (equation 1).

Figure 7C:
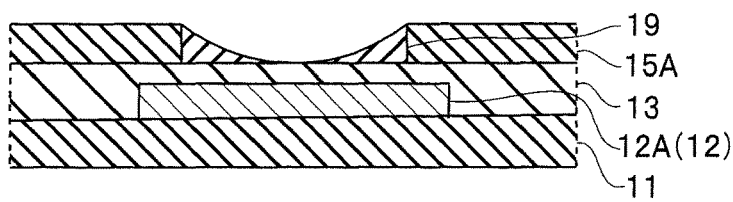
FIG. 7C is a partial sectional view for explaining the method for producing the ultrasound transducer element of the first embodiment.

Etch back processing is performed under dry etching conditions in which etching rates of the resist mask 63 and the gap adjusting layer 19A are equal to each other, whereby the gap adjusting portion 19 formed from a material with a high dielectric constant with a surface profile shown in (equation 1) is produced in the inside of the cavity forming portion 14A, as shown in FIG. 7C.

<Formation of Sacrifice Layer>

Figure 7D:
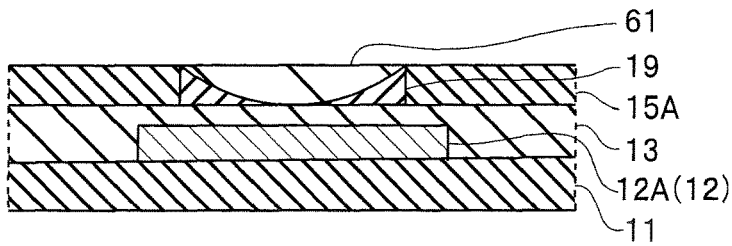
FIG. 7D is a partial sectional view for explaining the method for producing the ultrasound transducer element of the first embodiment.

A sacrifice layer material composed of tungsten, for example, is deposited to a thickness of the maximum thickness (TR) of the cavity forming portion 14A or more. Subsequently, when polishing by a CMP method is performed, a structure including a sacrifice layer 61 in a cavity shape is obtained as shown in FIG. 7D. A maximum thickness "t0 (TR)" of the sacrifice layer 61 after polishing is, for example, 0.05 μm to 0.3 μm and preferably is 0.05 μm to 0.15 μm.

<Formation of Upper Insulating Layer>

The upper insulating layer 15 is formed by a similar method and from a similar material to the lower insulating layer 13, for example. Subsequently, at a predetermined position of the upper insulating layer 15, an opening portion (not illustrated) into which an etchant is poured is formed in order to remove the sacrifice layer 61.

<Formation of Cavity>

The sacrifice layer 61 is selectively removed by etching, and thereby the cavity 14 is formed. When tungsten (W) is used as the sacrifice layer 61, and SiN is used as the lower insulating layer 13 and the upper insulating layer 15, for example, a hydrogen peroxide solution ($H_2O_2$) is used as the etchant. Further, when conductive polycrystalline silicon is used as the sacrifice layer 61, and SiN is used as the lower insulating layer 13 and the upper insulating layer 15, xenon fluoride gas ($XeF_2$) is used as the etchant.

<Formation of Upper Electrode Layer>

By a method similar to the method for forming the lower electrode layer 12, the upper electrode layer 16 is formed.

<Formation of Protection Layer>

Figure 7E:
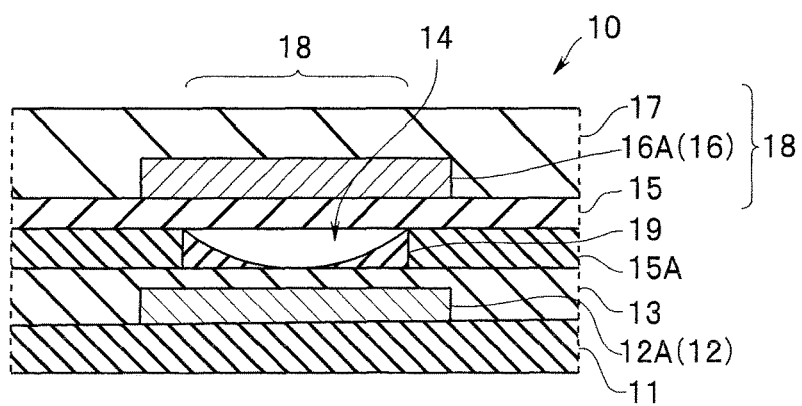
FIG. 7E is a partial sectional view for explaining the method for producing the ultrasound transducer element of the first embodiment.

As shown in FIG. 7E, the upper insulating layer 15 is covered with the protection layer 17. The protection layer 17 has not only a protection function, but also a function of connecting the plurality of US elements 20. The protection layer 17 is formed from a flexible resin such as polyimide, epoxy, acryl, or poly-para-xylene, and among them, polyimide is preferable since polyimide has high chemical resistance and flexibility, and is easy to process. Note that the protection layer 17 may be of a double layer structure in which a second insulating layer having biocompatibility is further formed on a first insulating layer.

Note that the plan view of the cavity 14 does not have to be perfect circular, but may be substantially circular. Further, the plan view of the cavity 14 may be in a polygonal shape that is substantially circular. Namely, a shape of the cavity forming portion 14A is not limited to a circular cylinder shape, and may be a polygonal column shape or the like. When the cavity forming portion 14A is in a polygonal column shape, shapes in plan view of the upper electrode portion 16A and the lower electrode portion 12A are preferably also made polygonal. In the gap adjusting portion 19, a range of an inscribed circle can satisfy the thickness distribution.

The plurality of US elements 20 are disposed by being bent into a radial shape in a connecting direction shown in FIG. 4, and thereby the US array 40 shown in FIG. 2 and FIG. 3 is produced. The US array 40 is joined to an outer circumferential face of a cylinder with a predetermined outside diameter, for example. Further, a coaxial cable bundle 35 is connected to the US array 40, and the US unit 30 is produced.

<Action of US Element/US Cell>

Next, an action of the US element 20 will be described with use of FIG. 8A and FIG. 8B. Note that in FIG. 8A and FIG. 8B, the lower insulating layer 13, the upper insulating layer 15, the protection layer 17 and the like are not shown, and explanation of an influence thereof will be omitted.

Figure 8A:
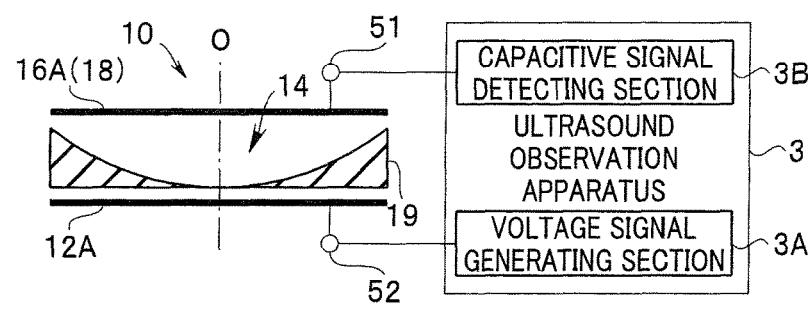
FIG. 8A is a schematic sectional view for explaining drive of the ultrasound transducer element of the first embodiment.
Figure 8B:
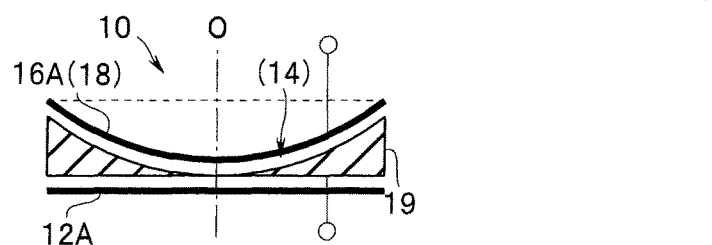
FIG. 8B is a schematic sectional view for explaining drive of the ultrasound transducer element of the first embodiment.

As shown in FIG. 8A, the lower electrode portion 12A is connected to a voltage signal generating section 3A of the ultrasound observation apparatus 3 via the lower electrode terminal 52. The upper electrode portion 16A is connected to a capacitive signal detecting section 3B via the upper electrode terminal 51 to be at a ground potential. The capacitive signal detecting section 3B detects a capacitive signal (a current change) at a time of receiving ultrasound.

At a time of ultrasound generation (drive time), the voltage signal generating section 3A applies a drive voltage signal including a bias voltage to the lower electrode portion 12A. When a voltage is applied to the lower electrode portion 12A, the upper electrode portion 16A at a ground potential is attracted to the lower electrode portion 12A by an electrostatic force as shown in FIG. 8B, and therefore the membrane 18 including the upper electrode portion 16A deforms into a concave shape. Note that the outer circumferential portion of the cavity 14 has a small height (thickness) "t", but does not interfere with deformation of the membrane 18, since a deformation amount of the outer circumferential portion of the membrane 18 is small.

When voltage application to the lower electrode portion 12A becomes nonexistent, the membrane 18 is restored to be in an original shape shown in FIG. 8A by an elastic force. Ultrasound is generated by vibration by (deformation/restoration) of the membrane 18.

Here, in the cavity 14 of the conventional US element, a whole of an inside thereof is made of air (vacuum) with a relative dielectric constant of "1", and the thickness thereof is the same and "t0" from the center portion to the outer circumferential portion. In other words, the cavity 14 of the conventional US element is the same as the cavity forming portion 14A of the US element 20.

In contrast with this, the gap adjusting portion 19 is placed in the inside of the cavity forming portion 14A of the US element 20. A relative dielectric constant Ks of the gap adjusting portion 19 formed from a material with a high dielectric coefficient is larger than "1". Therefore, a dielectric equivalent spacing "Teff" of the gap adjusting portion 19 is expressed by (equation 3) in a position at which the distance from a center of the cavity 14 is "r". Here, the dielectric equivalent spacing "Teff" is an electrostatic spacing with the relative dielectric constant Ks taken into consideration with respect to a physical spacing "T".

$$Teff(r)=Tr(r)/Ks \qquad \text{(Equation 3)}$$

Here, when the relative dielectric constant Ks is sufficiently larger than "1", for example, in the case of Ks≥3, the dielectric equivalent spacing "Teff" can be regarded as substantially "zero". Namely, in the US element 20, the gap adjusting portion 19 can be regarded as electrostatically absent.

Therefore, the dielectric equivalent spacing "teff" of the cavity 14 can be expressed by being approximated by (equation 4).

$$teff=t0-T(r) \qquad \text{(Equation 4)}$$

In other words, a physical spacing between the lower electrode portion 12A and the upper electrode portion 16A that are disposed to face each other via the cavity 14 is uniform. However, the dielectric equivalent spacing "Teff" that is an effective thickness of the cavity 14, namely, the electrostatic spacing (effective distance between the electrodes) is the maximum at a center (r=0), and decreases in a curved manner toward the outer circumferential portion. Since an electrostatic force is proportional to the effective distance between the electrodes, the electrostatic force that acts between the electrodes increases in the US element 20 more than in the conventional US element in which the distance between the electrodes is uniform. Therefore, the US element 20 has favorable generation efficiency of ultrasound.

Further, in the US element 20, an entire undersurface of the membrane 18 that is attracted to the lower electrode portion 12A deforms in such a manner as to contact and stretch onto the top surface of the gap adjusting portion 19, when driven. Therefore, the deformation state of the membrane 18 when driven becomes the same as the shape of the top surface of the gap adjusting portion 19 shown by (equation 1) and the like.

As already described, the shape shown by (equation 1) or the like is a theoretical deformation shape of the vibration film.

The ultrasound generated by the US cell 10 that deforms into a theoretical state becomes an ideal waveform with little distortion. Therefore, the US element 20 having the US cells 10 has favorable transmission efficiency of ultrasound.

Note that when the entire undersurface of the membrane 18 deforms significantly in such a manner as to stretch, namely, abut onto the top surface of the gap adjusting portion 19, a gas may be held in the inside in a compressed state when the gas is present in the cavity 14, or may be released to an outside via an opening portion (not illustrated) that is formed to cause an etchant to flow therein, for example.

Further, in the US element 20, the gap adjusting portion 19 formed from a material with a high dielectric coefficient with a higher insulating property than air is placed between the electrodes, and therefore, a withstand voltage between electrodes is high.

The US element 20 having the US cells 10 has favorable reception efficiency of ultrasound. As is already described, in the US cell 10 in which the distance between the electrodes decreases from the center portion to the outer circumferential portion, the electrostatic capacitance increases more than in the conventional US cell in which the distance between the electrodes is uniform. Therefore, in the US cell 10, a change rate of a charge amount increases even if the membrane 18 deforms to the extent that is the same as in the conventional US cell. Furthermore, the outer circumferential portion of the membrane 18 has a small deformation amount since the outer circumferential portion is restrained by the intermediate insulating layer 15A, but since the distance between the electrodes is short, the change in the charge amount is large.

As in the above explanation, the US element 20 has favorable transmission and reception efficiency of ultrasound. The US endoscope 2 including the US element 20 has favorable transmission and reception efficiency of ultrasound.

Modification of First Embodiment

Figure 9A:
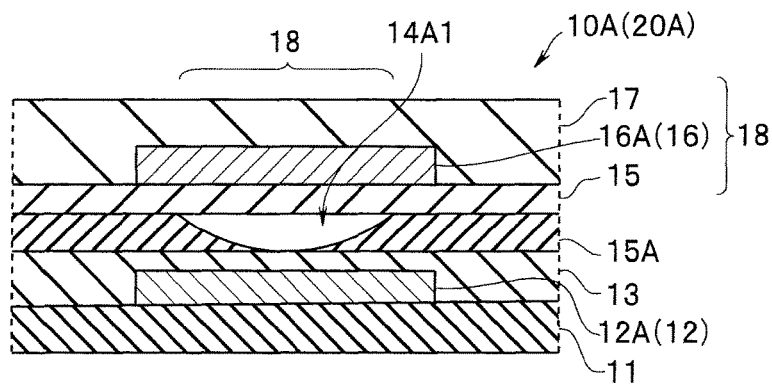
FIG. 9A is a partial sectional view of an ultrasound transducer element of modification 1 of the first embodiment.

As shown in FIG. 8A and the like, in the US element 20, the thickness of the cavity is varied because the gap adjusting portion 19 that is formed from a material with a high dielectric constant in the inside of the cavity forming portion 14A that is a cylindrical cavity portion formed in the intermediate insulating layer 15A is placed. In contrast with this, as in a US cell 10A shown in FIG. 9A, a part of the intermediate insulating layer 15A formed from a material with a high dielectric constant may be made a cavity 14A1 in which a thickness varies. Namely, a gap adjusting portion of a US element 20A of modification 1 of the first embodiment shown in FIG. 9A is a part of the intermediate insulating layer 15A.

Figure 9B:
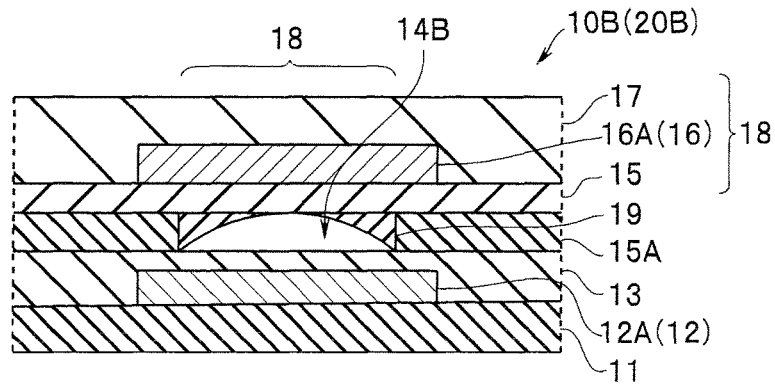
FIG. 9B is a partial sectional view of an ultrasound transducer element of modification 2 of the first embodiment.

Further, as shown in FIG. 9B, a cavity 14B of a US cell 10B of a US element 20B of modification 2 of the first embodiment is a so-called upward concave shape with a thickness thereof monotonously increasing in a curved manner toward an outer circumferential portion from a center portion similarly to that of the US element 20.

The US element 20A and the US element 20B have the same effect as the US element 20.

Second Embodiment

Hereinafter, with reference to the drawings, a US element 20C having a US cell 10C of a second embodiment will be described. Since the US cell 10C and the US element 20C are analogous to the US cell 10 and the US element 20 of the first embodiment, the same components will be assigned with the same reference signs, and explanation thereof will be omitted.

Figure 10A:
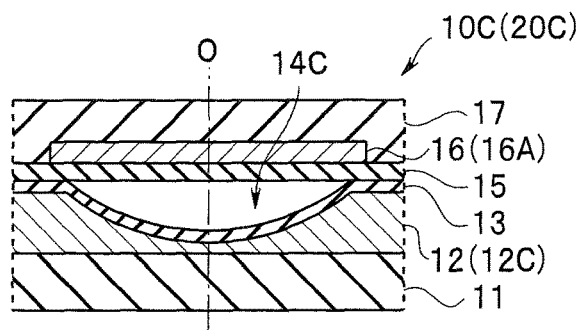
FIG. 10A is a partial sectional view of an ultrasound transducer element of a second embodiment.

As shown in FIG. 10A, in the US cell 10C, a thickness T12 of a lower electrode portion 12C that is covered with the lower insulating layer 13 increases monotonously in a curved manner toward an outer periphery from a center. Therefore, a physical spacing between the lower electrode portion 12C and the upper electrode portion 16A monotonously decreases in a curved manner toward an outer circumferential portion from a center. Therefore, a thickness "t" of a cavity 14C monotonously increases in a curved manner toward an outer circumferential portion from a center portion.

Distribution of the thickness T12 of the lower electrode portion 12C of the US element 20C and distribution of the thickness "t" of the cavity 14C can be shown by a Bessel function of the zeroth kind of (equation 1) or (equation 2) similarly to the thickness variation of the gap adjusting portion 19 of the US element 20 of the first embodiment. Namely, in the US element 20C, a variation state of the thickness of the cavity 14C is the same as a deformation state of a membrane when driven.

In other words, a top surface shape of the lower electrode portion 12C that is covered with the lower insulating layer 13 is the same as an undersurface shape of the cavity 14C.

The lower electrode portion 12C is formed by performing etch back processing with use of a resist mask or the like in which a thickness monotonously increases toward an outer circumferential portion from a center portion similarly to the gap adjusting layer 19A.

Modification of Second Embodiment

Figure 10B:
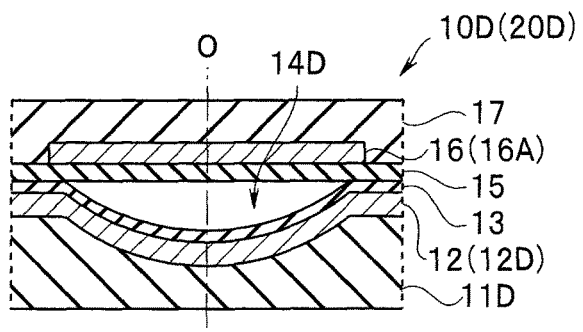
FIG. 10B is a partial sectional view of an ultrasound transducer element of modification 1 of the second embodiment.

As shown in FIG. 10B, in a US cell 10D of a US element 20D of modification 1 of the second embodiment, a convex portion a depth of which is expressed by a Bessel function of the zeroth kind, and monotonously decreases toward an outer circumferential portion from a center portion is formed in a substrate 11D, and a lower electrode portion 12D is formed thereon. Therefore, a physical spacing between the lower electrode portion 12D and the upper electrode portion 16D monotonously decreases in a curved manner toward the outer circumferential portion from a center. A thickness "t" of a cavity 14D monotonously increases in a curved manner toward the outer circumferential portion from the center portion.

Figure 10C:
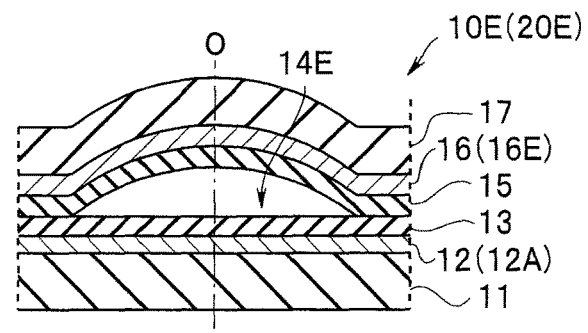
FIG. 10C is a partial sectional view of an ultrasound transducer element of modification 2 of the second embodiment.

Further, in a US cell 10E of a US element 20E of modification 2 of the second embodiment shown in FIG. 10C, an upper electrode portion 16E is deformed into a convex shape that is expressed by a Bessel function of the zeroth kind by an internal stress of the membrane 18. Therefore, a physical spacing between the lower electrode portion 12A and an upper electrode portion 16E monotonously decreases in a curved manner toward an outer circumferential portion from a center. Therefore, a thickness "t" of a cavity 14E monotonously decreases in a curved manner toward the outer circumferential portion from the center portion.

Figure 10D:
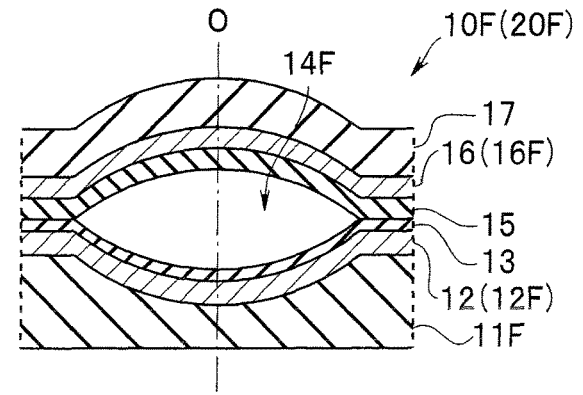
FIG. 10D is a partial sectional view of an ultrasound transducer element of modification 3 of the second embodiment.

Furthermore, a US cell 10F of a US element 20F of modification 3 of the second embodiment shown in FIG. 10D has a cavity 14F in a double convex shape by a cavity in a downward convex shape that is expressed by a Bessel function of the zeroth kind, and a cavity in an upward convex shape that is expressed by a Bessel function of the zeroth kind being combined. A physical spacing between an upper electrode portion 16F and a lower electrode portion 12F on a substrate 11F monotonously decreases in a curved manner toward an outer circumferential portion from a center.

The US elements 20C to 20F all have the same effect as the US element 20. Further, unlike the US element 20, the US elements 20C to 20F are easily produced since formation of the gap adjusting portion 19 is not necessary.

As described above, the US elements 20A to 20F have favorable ultrasound transmission and reception efficiency similarly to the US element 20. The US endoscopes 2A to 2F including the US elements 20A to 20F have favorable ultrasound transmission and reception efficiency.

Note that depending on the restraint conditions of the outer periphery of the membrane 18, the thickness (height) distribution t(r) of the cavities 14 to 14F shown in the first embodiment, the second embodiment and the modifications may be expressed by an arc function shown in (equation 5) or a sine function shown in (equation 6) if the thickness (height) distribution t(r) can be expressed by a function of the thickness "t" monotonously decreasing in a curved manner with increase of [r].

$$t(r)=t0\times[1-(r/R)^2] \tag{Equation 5}$$

$$t(r)=t0\times[1-\sin(\pi/2\times r/R)] \tag{Equation 6}$$

Further, the shape of the cavity is not limited to the shapes of the cavities 14 to 14F, and the thickness of the cavity may monotonously decrease in a curved manner toward the outer circumferential portion from the center portion. For example, the top surface of the cavity may be bent significantly while the undersurface may be bent a little. Contrary to this, the top surface of the cavity may be bent a little, while the undersurface may be bent significantly.

The present invention is not limited to the aforementioned embodiments, and various modifications, alterations and the like can be made within the range without departing from the gist of the present invention.

What is claimed is:

1. An ultrasound transducer element, comprising:
   a plurality of electrostatic capacitance type ultrasound cells each comprising:
   a lower electrode portion;
   a membrane comprising an upper electrode portion, wherein the lower electrode portion and the membrane are oriented and disposed via a cavity circular in plain view; and
   between the lower electrode portion and the upper electrode portion, a gap adjusting portion comprising a dielectric,
      wherein a thickness of the gap adjusting portion monotonously increases in a curved manner toward an outer circumferential portion of the gap adjusting portion from a center portion of the gap adjusting portion, and
      wherein a thickness of the cavity monotonously decreases in a curved manner toward an outer circumferential portion of the cavity from a center portion of the cavity,
   wherein the lower electrode portion, the membrane, and the gap adjusting portion of the each of the electrostatic capacitance type ultrasound cells are configured such that:
      when a drive voltage signal is applied, an entire undersurface of the membrane that is attracted to the lower electrode portion deforms in such a manner as to contact and stretch onto a top surface of the gap adjusting portion, and a three-dimensional deformation state of the membrane becomes substantially the same as a three-dimensional shape of the top surface of the gap adjusting portion, and
      when application of the drive voltage signal becomes nonexistent, the membrane is restored to be in an original shape by an elastic force and ultrasound is generated.

2. The ultrasound transducer element according to claim 1,
   wherein a variation state of the thickness of the cavity when the drive voltage signal is applied is expressed by an arc function.

3. The ultrasound transducer element according to claim 1,
   wherein a variation state of the thickness of the cavity when the drive voltage signal is applied is expressed by a sine function.

4. The ultrasound transducer element according to claim 1,
   wherein a variation state of the thickness of the cavity when the drive voltage signal is applied is expressed by a zeroth-order Bessel function.

5. The ultrasound transducer element according to claim 1,
   wherein the membrane further comprises an opening portion via which gas present in the cavity is released to an outside.

6. The ultrasound transducer element according to claim 1,
   wherein a relative dielectric constant of the dielectric is three or more.

7. An ultrasound endoscope comprising:
   an ultrasound transducer element comprising:
      a plurality of electrostatic capacitance type ultrasound cells each comprising:
      a lower electrode portion;
      a membrane comprising an upper electrode portion, wherein the lower electrode portion and the membrane are oriented and disposed via a cavity circular in plain view; and
      between the lower electrode portion and the upper electrode portion, a gap adjusting portion comprising a dielectric,
         wherein a thickness of the gap adjusting portion monotonously increases in a curved manner toward an outer circumferential portion of the gap adjusting portion from a center portion of the gap adjusting portion, and
         wherein a thickness of the cavity monotonously decreases in a curved manner toward an outer circumferential portion of the cavity from a center portion of the cavity,
      wherein the lower electrode portion, the membrane, and the gap adjusting portion of the each of the electrostatic capacitance type ultrasound cells are configured such that:
         when a drive voltage signal is applied, an entire undersurface of the membrane that is attracted to the lower electrode portion deforms in such a manner as to contact and stretch onto a top surface of the gap adjusting portion, and a three-dimensional deformation state of the membrane becomes substantially the same as a three-dimensional shape of the top surface of the gap adjusting portion, and
         when application of the drive voltage signal becomes nonexistent, the membrane is restored to be in an original shape by an elastic force and ultrasound is generated.

8. The ultrasound endoscope according to claim 7,
   wherein a variation state of the thickness of the cavity when the drive voltage signal is applied is expressed by an arc function.

9. The ultrasound endoscope according to claim 7,
wherein a variation state of the thickness of the cavity when the drive voltage signal is applied is expressed by a sine function.

10. The ultrasound endoscope according to claim 7,
wherein a variation state of the thickness of the cavity when the drive voltage signal is applied is expressed by a zeroth-order Bessel function.

11. The ultrasound endoscope according to claim 7,
wherein the membrane further comprises an opening portion via which gas present in the cavity is released to an outside.

12. The ultrasound endoscope according to claim 7,
wherein a relative dielectric constant of the dielectric is three or more.

* * * * *